(12) United States Patent
Suneshine et al.

(10) Patent No.: US 11,116,567 B2
(45) Date of Patent: *Sep. 14, 2021

(54) CAUTERY DEVICE

(71) Applicant: Single Pass, LLC, Lake Forest, CA (US)

(72) Inventors: Peter J. Suneshine, Paradise Valley, AZ (US); Kevin Hirsch, Phoenix, AZ (US); Bryan D. Knodel, Flagstaff, AZ (US)

(73) Assignee: Single Pass, LLC, Lake Forest, CA (US)

( * ) Notice: Subject to any disclaimer, the term of this patent is extended or adjusted under 35 U.S.C. 154(b) by 648 days.

This patent is subject to a terminal disclaimer.

(21) Appl. No.: 15/871,787

(22) Filed: Jan. 15, 2018

(65) Prior Publication Data

US 2018/0132929 A1   May 17, 2018

Related U.S. Application Data

(63) Continuation of application No. 15/256,336, filed on Sep. 2, 2016, now Pat. No. 9,901,393.

(60) Provisional application No. 62/253,130, filed on Nov. 9, 2015.

(51) Int. Cl.
*A61B 18/14* (2006.01)
*A61B 18/12* (2006.01)
*A61B 18/00* (2006.01)
*A61B 17/00* (2006.01)
*A61B 18/16* (2006.01)

(52) U.S. Cl.
CPC ...... *A61B 18/1477* (2013.01); *A61B 18/1206* (2013.01); *A61B 2017/00734* (2013.01); *A61B 2018/00178* (2013.01); *A61B 2018/00595* (2013.01); *A61B 2018/1226* (2013.01); *A61B 2018/1425* (2013.01); *A61B 2018/162* (2013.01)

(58) Field of Classification Search
CPC ............ A61B 18/1206; A61B 18/1477; A61B 2017/00734; A61B 2018/00178; A61B 2018/00595; A61B 2018/1226; A61B 2018/1425; A61B 2018/162
See application file for complete search history.

(56) References Cited

U.S. PATENT DOCUMENTS 3,598,108 A    8/1971   Jamshidi et al.
4,196,734 A *  4/1980   Harris ................ A61B 18/1206
                                                        219/233

(Continued)

FOREIGN PATENT DOCUMENTS

EP    2319443 A1   5/2011
WO    97/15237 A1  5/1997

*Primary Examiner* — Michael F Peffley
*Assistant Examiner* — Amanda L Zink
(74) *Attorney, Agent, or Firm* — Patterson + Sheridan, LLP

(57) ABSTRACT

Techniques are disclosed to cauterize tissue. For example, certain aspects herein relate to a cautery device. The cautery device includes a voltage source comprising a voltage pump and a battery. The cautery device further includes a probe for applying current from the voltage source to tissue. The probe includes a first electrically conductive element electrically coupled to a first pole of the voltage source. The probe further includes a second electrically conductive element coupled to a second pole of the voltage source.

4 Claims, 12 Drawing Sheets

(56) References Cited

U.S. PATENT DOCUMENTS

| | | | |
|---|---|---|---|
| 4,269,174 A * | 5/1981 | Adair | A61B 18/082 |
| | | | 128/842 |
| 4,878,493 A * | 11/1989 | Pasternak | A61B 18/12 |
| | | | 607/99 |
| 5,472,441 A * | 12/1995 | Edwards | A61N 5/045 |
| | | | 606/41 |
| 5,578,030 A | 11/1996 | Levin | |
| 5,792,138 A * | 8/1998 | Shipp | A61B 18/12 |
| | | | 429/61 |
| 5,928,163 A | 7/1999 | Roberts et al. | |
| 6,106,524 A * | 8/2000 | Eggers | A61B 5/0531 |
| | | | 606/41 |
| 6,402,742 B1 * | 6/2002 | Blewett | A61B 18/1206 |
| | | | 606/34 |
| 6,451,017 B1 * | 9/2002 | Moutafis | A61B 17/32037 |
| | | | 604/35 |
| 6,592,530 B1 | 7/2003 | Farhadi | |
| 2003/0093007 A1 | 5/2003 | Wood | |
| 2003/0109802 A1 | 6/2003 | Laeseke et al. | |
| 2004/0215178 A1 | 10/2004 | Maurice | |
| 2005/0203441 A1 | 9/2005 | Voegele | |
| 2007/0118112 A1 | 5/2007 | Kennedy | |
| 2007/0213703 A1 | 9/2007 | Naam et al. | |
| 2008/0269862 A1 | 10/2008 | Elmouelhi et al. | |
| 2009/0259225 A1 | 10/2009 | Ravikumar et al. | |
| 2012/0226190 A1 | 9/2012 | Tan | |
| 2014/0276750 A1 | 9/2014 | Gilbert | |
| 2015/0148800 A1 | 5/2015 | Ravikumar et al. | |
| 2016/0067497 A1 * | 3/2016 | Levine | A61B 5/4836 |
| | | | 607/62 |

* cited by examiner

CAUTERY DEVICE

CROSS-REFERENCE TO RELATED APPLICATIONS

This application is a continuation application of U.S. patent application Ser. No. 15/256,336 filed Sep. 2, 2016, granted as U.S. Pat. No. 9,901,393 on Feb. 27, 2018, which claims priority to Provisional Patent Application No. 62/253,130 filed Nov. 9, 2015. The content of each of these applications is hereby incorporated by reference in its entirety.

BACKGROUND

Field

Embodiments of the invention generally relate to techniques for cauterizing tissue. More specifically, embodiments presented herein are directed to a battery powered bipolar cautery device.

Description of the Related Art

Cauterization of tissue can be used in surgeries, emergency circumstances, etc. to stop bleeding, prevent infections, and minimize potential medical harm. Accordingly, cauterization can play an important role in a number of potentially life threatening situations.

For example, invasive procedures on living creatures (e.g., humans and animals) may be necessary to diagnose or treat certain diseases or infections. In some cases, such invasive procedures may be performed by introducing a needle into the human or animal. Such a needle may be a guide needle, which has a hollow core, or lumen, throughout the length of the needle. Such a guide needle may allow other instruments to be inserted into the human or animal to allow the invasive procedure to be performed.

For example, a biopsy may need to be performed to make a diagnosis of cancer, an infectious disease, or an inflammatory disease. A biopsy may include removing tissues from an organ or an abnormal lesion from an individual. With the advent of image guidance, minimally invasive biopsy techniques may be used to perform the biopsy. For example, a guide needle may be inserted and guided by a surgeon to the organ or lesion. Further, a biopsy needle may be introduced within the lumen of the guide needle to collect the needed tissue sample. Accordingly, a biopsy may be performed through only a tiny puncture in the patient's skin (e.g., percutaneously).

Such minimally invasive techniques performed through the guide needle, however, mean that there is a lack of open access to the tissue where the procedure is performed, and accordingly, it may be difficult to diagnose if there is a clinically relevant hemorrhage at the site of the procedure. For example, sheared blood vessels including arteries may be difficult to see using imaging techniques. Accordingly, homeostasis of the tissue, such as by cauterization, may be difficult to achieve at the time the procedure is performed. Current techniques for homeostasis of tissue, such as manual pressure, adrenaline injection, coagulated autologous blood products, gel foam slurry, biocompatible plugs, glue, etc. have proved ineffective in certain situations for dealing with such issues.

In other examples, cauterization may be needed for other situations beyond such percutaneous procedures, such as emergency cauterization due to an open wound, loss of limbs, etc. For example, cauterization may also be used in open body procedures in the outpatient setting, or in an ambulance.

SUMMARY

One embodiment presented herein includes a cautery device. The cautery device includes a probe shaped to fit inside a lumen of a guide needle. The probe includes a first electrically conductive element exposed at one end of the probe. The first electrically conductive element is electrically coupled to a first pole of a voltage source. The cautery device further includes a second electrically conductive element configured to electrically couple with the guide needle. The second electrically conductive element is further electrically coupled to a second pole of the voltage source. The cautery device further includes a fitting configured to receive the guide needle.

Another embodiment presented herein includes a method of cauterizing. The method includes introducing a probe into a lumen of a guide needle. The probe includes a first electrically conductive element exposed at one end of the probe. The first electrically conductive element is electrically coupled to a first pole of a voltage source. The guide needle is electrically coupled to a second pole of the voltage source. The method further includes creating an electric current through tissue via the first electrically conductive element and the guide needle. The method further includes cauterizing the tissue with the electric current.

Another embodiment presented herein includes a cautery device. The cautery device includes a probe shaped to fit inside a lumen of a guide needle. The probe includes a first electrically conductive element exposed at one end of the probe. The first electrically conductive element is electrically coupled to a first pole of a voltage source comprising a voltage pump and a battery. The cautery device further includes a second electrically conductive element configured to electrically couple with the guide needle. The second electrically conductive element is further electrically coupled to a second pole of the voltage source. The cautery device further includes a fitting configured to receive the guide needle. The cautery device is a self-contained handheld device. The cautery device is configured to create an electric current through tissue via the first electrically conductive element and the second electrically conductive element.

Another embodiment presented herein includes a cautery device. The cautery device includes a voltage source comprising a voltage pump and a battery. The cautery device further includes a probe for applying current from the voltage source to tissue. The probe includes a first electrically conductive element electrically coupled to a first pole of the voltage source. The probe further includes a second electrically conductive element coupled to a second pole of the voltage source.

Another embodiment presented herein includes a method of cauterizing. The method includes generating, by a voltage source comprising a battery and a voltage pump, a DC signal at a first voltage based on the battery being at a second voltage, the first voltage being higher than the second voltage. The method further includes applying the DC signal to tissue to cauterize the tissue via a probe electrically coupled to the voltage source. The probe includes a first electrically conductive element electrically coupled to a first pole of the voltage source. The probe further includes a second electrically conductive element coupled to a second pole of the voltage source.

BRIEF DESCRIPTION OF THE DRAWINGS

So that the manner in which the above recited aspects are attained and can be understood in detail, a more particular description of embodiments of the invention, briefly summarized above, may be had by reference to the appended drawings.

Note, however, that the appended drawings illustrate only typical embodiments of this invention and are therefore not to be considered limiting of its scope, for the invention may admit to other equally effective embodiments.

DETAILED DESCRIPTION

Figure 1:
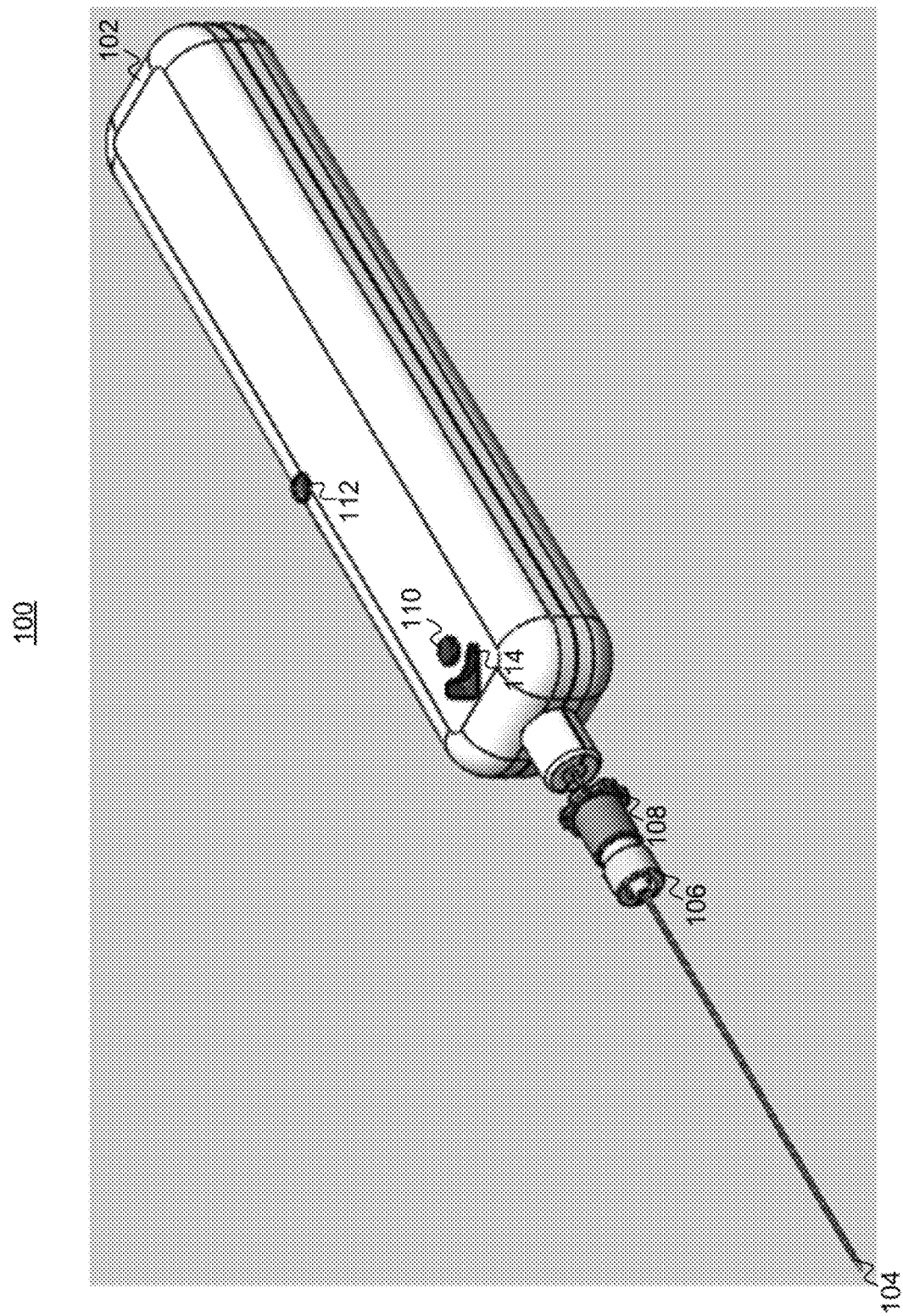
FIGS. 1 and 1A illustrate external views of an example of a bipolar cautery device, according to one embodiment.

The following description and the accompanying figures, which describe and show certain embodiments, are made to demonstrate several possible configurations a cautery device can take to include various aspects and features. Some embodiments presented herein provide techniques to cauterize tissue. In particular, certain embodiments are described herein with respect to a battery powered bipolar cautery device. Such a battery powered bipolar cautery device, unlike large cautery devices that require plugging into a large power source (e.g., AC power from an outlet) may, in certain embodiments, advantageously be handheld and portable, and therefore usable in a variety of circumstances (e.g., emergency situations where a large wall plug-in device is not available or usable). For example, a battery powered bipolar cautery device, as detailed herein, may be used in the field, where no AC power source is available to run a standard bipolar cautery. Further, a battery powered bipolar cautery device, as detailed herein may also be used in clinical settings where the routine use of a heavy immobile bipolar generator is not feasible, impractical, or difficult.

Further, such a battery powered bipolar cautery device may enable bipolar cauterization even with a battery powered (e.g., handheld) device. Bipolar cauterization may be advantageous over thermal cauterization through a heating element (e.g., manually heated cauterizing element, electrical cauterizing element configured to generate heat, etc.) as the bipolar cauterization may be performed more quickly and more accurately such that targeted tissues are cauterized and there is minimal impact to other surrounding tissues.

Such bipolar cauterization of tissue may be performed by creating a current through the tissue which may utilize a voltage source with a high voltage. In some embodiments, such a voltage may not be able to be provided by a battery alone. Accordingly, some embodiments herein further include a voltage pump configured to increase the voltage of a battery in the bipolar cautery device so as to apply a higher voltage to the tissue to cauterize the tissue. The voltage pump is advantageously designed to increase the voltage of the battery and supply a continuous current to the tissue during operation of the bipolar cautery device. In certain embodiments, the design of the voltage pump enables the battery powered bipolar cautery device to supply sufficient voltage, while still being powered by a battery source (e.g., a small battery source, such as, ~15V). Therefore, in certain aspects, the voltage pump allows the battery powered bipolar cautery device to be designed as a handheld device.

In certain embodiments, the bipolar cautery device is configured to cauterize tissue along a tract of a guide needle inserted in the tissue. In certain embodiments, the bipolar cautery device includes a probe shaped to fit inside a lumen of a guide needle. The probe includes an electrically conductive element that is electrically coupled to a first pole of a voltage source (e.g., battery). Further, in certain embodiments, the bipolar cautery device includes a second electrically conductive element configured to electrically couple the guide needle to a second pole of the voltage source. The bipolar cautery device may further include a fitting to secure the guide needle to the bipolar cautery device. The bipolar cautery device may be used in any appropriate application, such as, open body procedures, percutaneous procedures, etc.

In some embodiments, the probe of the bipolar cautery device is inserted into a lumen of a guide needle, such as after a biopsy is performed using the guide needle, and used to cauterize tissue along a tract created by the guide needle. In particular, an electric current may be generated by the voltage source, and accordingly the current flows from the probe to the guide needle through the tissue along the tract. The current flowing through the tissue may cause the tissue to be cauterized as the electrical resistance of the tissue itself causes it to generate heat (as opposed to the bipolar cautery device itself generating heat to cauterize the tissue), which cauterizes the tissue. The guide needle with the probe of the bipolar cautery device inserted in the lumen of the guide needle may be removed from the tissue by a surgeon moving it back along the tract and cauterizing the tissue along the tract as the guide needle and bipolar cautery device are moved along the tract.

Such use of a bipolar cautery device that fits within a lumen of a guide needle may provide several advantages for cauterizing tissue. For example, by creating a bipolar cautery device that can be introduced via an already inserted guide needle, the cauterization can be performed without additional invasive procedures into the tissues, and is also localized to the appropriate tissues. Further, in some embodiments, the bipolar cautery device described herein is a battery powered and handheld device for ease of use. In particular, inserting and removing the bipolar cautery device may be performed manually (e.g., by a surgeon) and therefore the device may be small and light enough to be easily manipulated manually. It should be noted that though embodiments described with respect to the bipolar cautery device including a probe shaped to fit inside a lumen of a guide needle are described as battery powered cautery devices, in some embodiments, such a bipolar cautery device may be powered by another power source (e.g., AC from a power outlet).

Accordingly, systems and methods are described herein for a bipolar cautery device. Those of skill in the art will recognize that the disclosed aspects and features are not limited to the examples described herein.

Figure 1A:
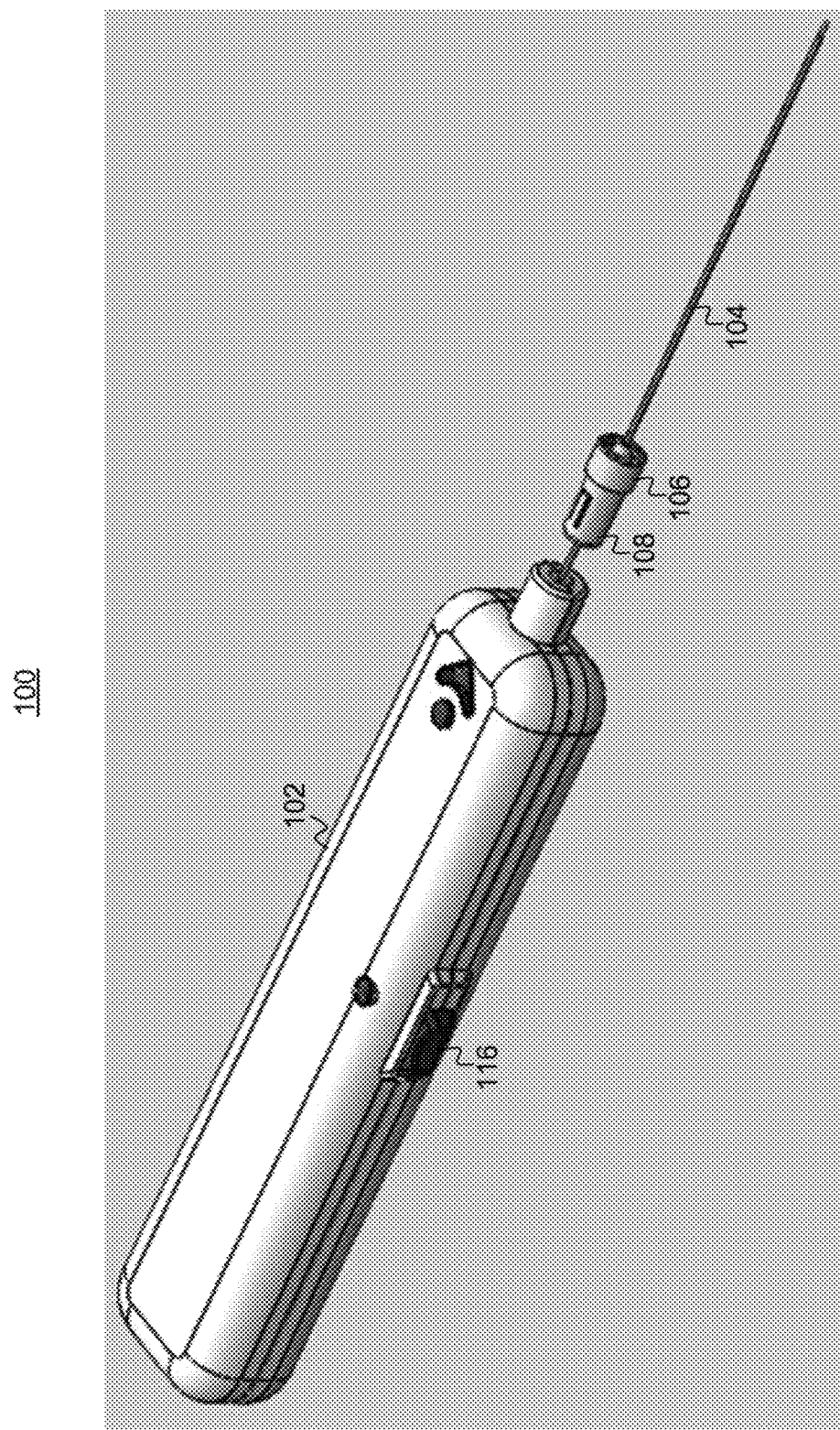

FIGS. 1 and 1A illustrate external views of an example of a bipolar cautery device 100, according to one embodiment. As shown, the bipolar cautery device 100 includes a housing 102, a probe 104, and a fitting 106. The housing 102 is configured to include components of the bipolar cautery device 100 configured to generate a current. In particular, the housing 102 may include a voltage source (e.g., a battery, a voltage pump, etc.). Further, the housing 102 may include controls (e.g., buttons, switches, etc.) that may be used to operate the bipolar cautery device 100. The housing 102 may further include indicators (e.g., light indicators) that visually indicate operation or functioning of the bipolar cautery device 100. In some embodiments, the housing may be a hand-held housing. The probe 104 has a length that extends from the housing 102.

For example, the housing 102 may include a button 110 that is configured to selectively enable or disable current from flowing through the probe 104. For example, the button 110 may control a switch that selectively couples the output of a voltage pump to the probe 104. The housing 102 may further include a switch 116 that powers on and off the bipolar cautery device 100. For example, the switch 116 may selectively couple an input of a voltage pump to an output of a battery or other appropriate voltage source.

The housing 102 may further include indicators 112 and 114. The indicator 112 may indicate if the bipolar cautery device 100 is on or not (e.g., the switch 116 is activated or not). The indicator 114 may indicate if current flow through the probe 104 is enabled or not (e.g., the button 110 is activated or not).

Figure 2:
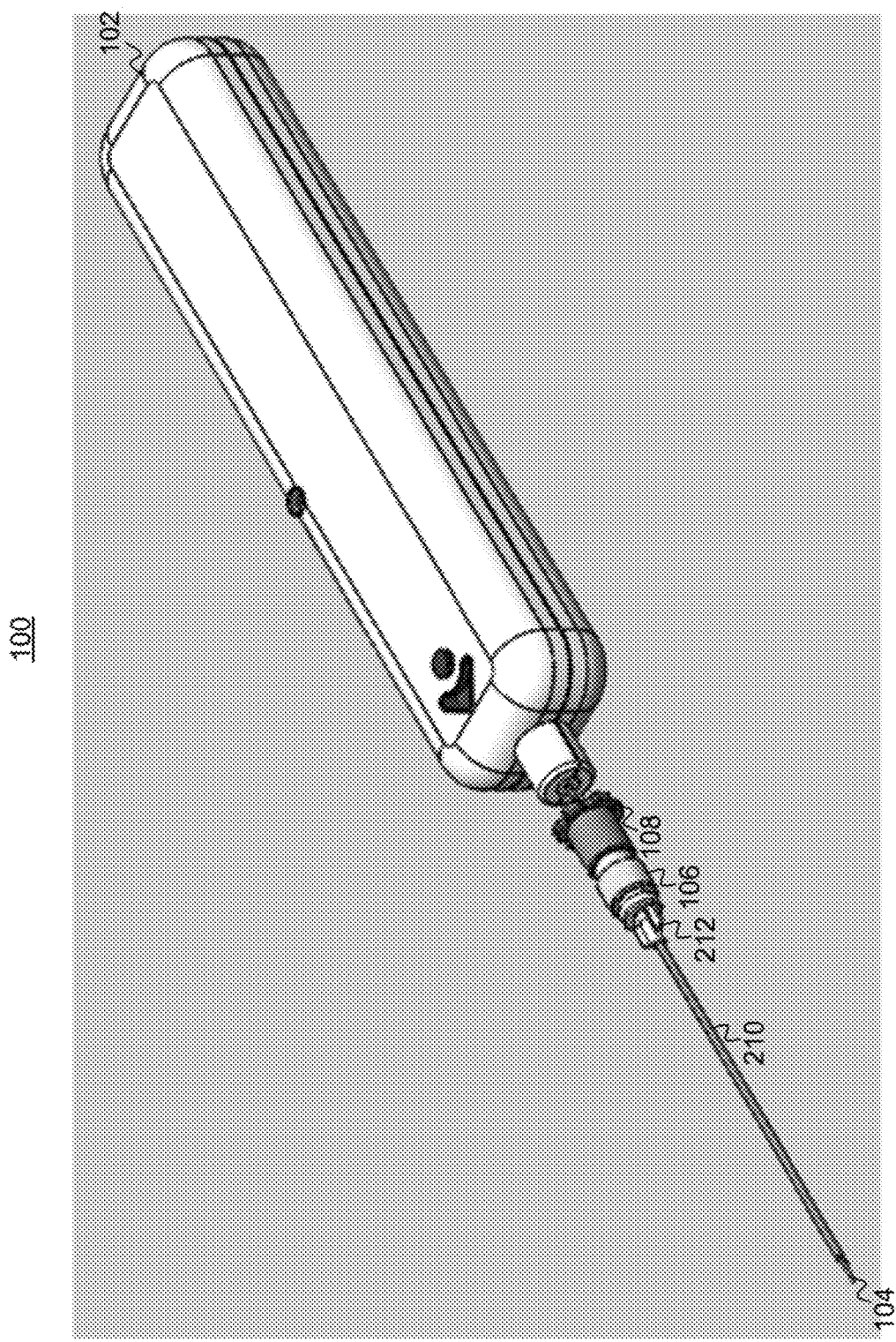
FIG. 2 illustrates an external view of the bipolar cautery device of FIGS. 1 and 1A with a guide needle secured thereon, according to one embodiment.

The fitting 106 is configured to secure a guide needle to the bipolar cautery device 100. For example, the fitting 106 may comprise a luer fitting configured to receive the guide needle 210 as shown in FIG. 2. The guide needle 210 may further comprise a fitting 212 (e.g., luer fitting) that is configured to secure the guide needle 210 to the fitting 106. The fitting 106 may further comprise a locking mechanism (e.g., threads of a screw mechanism, etc.) and the fitting 212 may comprise a corresponding locking mechanism (e.g., complementary threads of a screw mechanism, etc.) that locks with the locking mechanism of the fitting 106.

For example, the fitting 106 may comprise a male-fitting, and the guide needle 210 may comprise the corresponding female-fitting to the male fitting. The probe 104 is configured to fit through a lumen of the guide needle 210, and the guide needle 210 may slide along a length of the probe 104 and be secured to the fitting 106. For example, the probe 104 may have a diameter that is smaller than the diameter of the lumen of the guide needle 210. The guide needle 210 may be a standard guide needle used in the medical field. For example, the needle portion of the guide needle 210 may be made of an appropriate metal. Further, the fitting 212 may be made of a plastic material.

Figure 3:
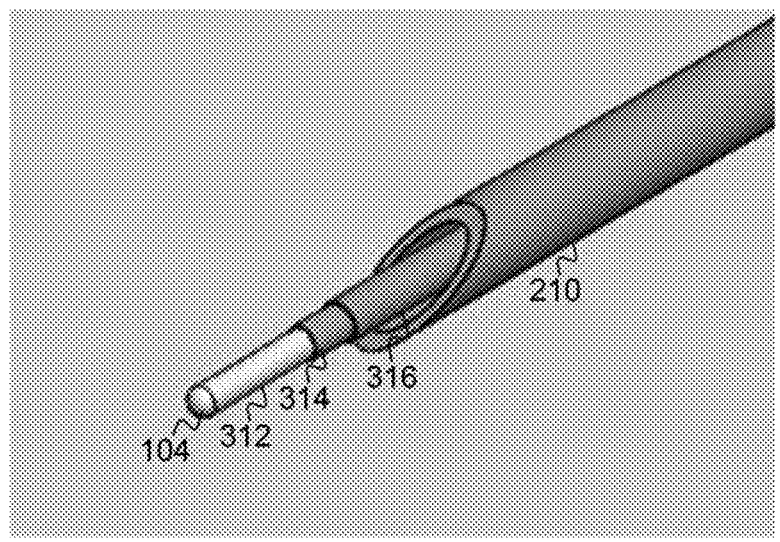
FIG. 3 illustrates an external view of a tip of the bipolar cautery device of FIGS. 1 and 1A with a guide needle secured thereon, according to one embodiment.

The fitting 106 may further include an interface 108. The interface 108 may be configured to couple the fitting to the probe 104. For example, the fitting 106 may be movable along a length of the probe 104 to a desired position. In particular, the fitting 106 may be moved to a position along the probe 104 such that when the guide needle 210 is secured to the fitting 106, a tip of the probe 104 may extend beyond the guide needle 210, such as shown in FIG. 3. The interface 108 may then be locked to the probe 104 at the desired position. The interface 108 may comprise, for example, a clamping mechanism configured to selectively clamp the fitting 106 to the probe 104.

The probe 104 comprises a conductive element, such as a metal wire 312 (e.g., 18 gauge or 20 gauge wire) having a length that extends from the housing 102. In some embodiments, the metal wire 312 may run the entire length of the probe 104 extending from the housing 102. The probe 104 further comprises an insulator 314 (e.g., sterilized polyimide or other thin insulator) positioned around the metal wire 312. Accordingly, the insulator 314 may cover a portion of the metal wire 312. For example, the insulator 314 may comprise an insulating tube. The insulator 314 may be configured to run along a length of the metal wire 312 of the probe 104. Further, as shown in FIG. 3 the insulator 314 may not cover and therefore expose a portion (e.g., tip) of the metal wire 312. Accordingly, the insulator 314 may not run the entire length of the metal wire 312 extending from the housing 102, but instead a shorter length than the metal wire 312 so as to expose a portion of the metal wire 312. In some embodiments, the probe 104 further comprises another conductive element, such as the metal outer portion 316 formed around the insulator 314. The metal outer portion 316 may comprise a metal tube that runs along a length of the insulator 314. As shown, the metal outer portion 316 may not run the entire length of the metal wire 312 or the insulator 314 extending from the housing 102, but instead a shorter length than the insulator 314. In particular, the metal outer portion 316 may be electrically insulated/isolated from the metal wire 312 along the length of the probe 104 extending from the housing 102.

As discussed, the housing 102 may include a voltage source. The voltage source may comprise a first pole (e.g., positive or negative pole) and a second pole (e.g., the other of the positive and negative pole). The metal wire 312 may be electrically coupled to the first pole of the voltage source, and the metal outer portion 316 may be electrically coupled to the second pole of the voltage source. For example, each of the metal wire 312 and metal outer portion 316 may extend into the housing 102 and then be separately coupled by metal contacts, wires, traces, etc., to the voltage source.

As shown, the metal outer portion 316 may be in contact with an inner wall of the guide needle 210 when the probe 104 is inserted in the lumen of the guide needle 210. Accordingly, the metal outer portion 316 may electrically couple to the guide needle 210, and therefore, the guide needle 210 may be electrically coupled with the second pole of the voltage source.

Accordingly, when the probe 104 is inserted in the guide needle 210, and the guide needle 210 is inserted in tissue, a current may be generated by the voltage source and pass through the metal wire 312 and the guide needle 210 (e.g., via the metal outer portion 316) via the tissue, and therefore cauterize the tissue. As discussed above, the metal wire 312 and metal outer portion 316/guide needle 210 may be insulated from each other via the insulator 314 to prevent a short in the circuit with the voltage source.

In the above described embodiment, the probe 104 is described as shaped to fit within a guide needle 210, and a fitting 106 is described to secure the guide needle 210 to the bipolar cautery device 100. However, in other embodiments, the probe 104 may have a different size or shape (e.g., formed as clamps, as separate wires, as a forked set of conductors, etc.). For example, the probe 104 may include a first conductive element electrically coupled to a first pole of a voltage source, and a second conductive element (e.g., insulated from the first conductive element) electrically coupled to a second pole of the voltage source. The first conductive element and second conductive element may be applied to tissue to pass a current from the first conductive element through the tissue to the second conductive element to cauterize the tissue. The voltage source in such embodiments may comprise a battery and voltage pump configured to cauterize tissue using battery power.

Figure 4:
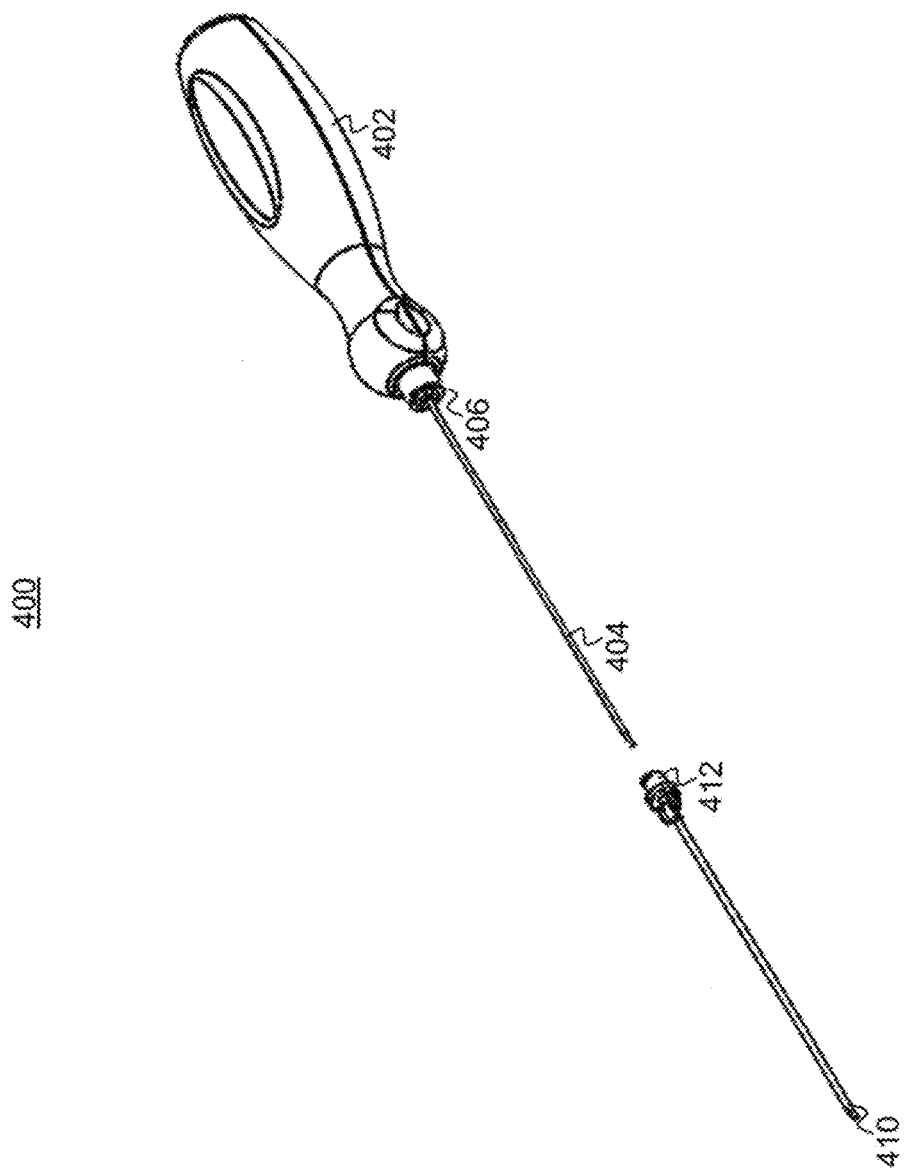
FIG. 4 illustrates an external view of another example of a bipolar cautery device, according to one embodiment.

FIG. 4 illustrates an external view of another example bipolar cautery device 400, according to one embodiment. The bipolar cautery device 400 includes a housing 402, a probe 404, and a fitting 406. The housing 402 may be similar to the housing 102 described with respect to FIGS. 1-3. In particular, the housing 402 is configured to include components of the bipolar cautery device 400 configured to generate a current. In particular, the housing 402 may include a voltage source (e.g., a battery, a voltage pump, etc.). Further, the housing 402 may include controls (e.g., buttons, switches, etc.) that may be used to operate the bipolar cautery device 400. The housing 402 may further include indicators (e.g., light indicators) that visually indicate operation or functioning of the bipolar cautery device 400. In some embodiments, the housing may be a hand-held housing. The probe 404 has a length that extends from the housing 402.

For example, the housing 402 may include a button that is configured to selectively enable or disable current from flowing through the probe 404. For example, the button may control a switch that selectively couples the output of a voltage pump to the probe 404. The housing 402 may further include a switch that powers on and off the bipolar cautery device 400. For example, the switch may selectively couple an input of a voltage pump to an output of a battery or other appropriate voltage source.

The housing 402 may further include indicators. The indicators may indicate if the bipolar cautery device 100 is on or not (e.g., the switch is activated or not) and/or if current flow through the probe 404 is enabled or not (e.g., the button is activated or not).

The fitting 406 may be configured to secure a guide needle 410 to the bipolar cautery device 400. For example, the fitting 406 may comprises a luer fitting configured to receive the guide needle 410. The guide needle 410 may further comprise a fitting 412 (e.g., luer fitting) that is configured to secure the guide needle 410 to the fitting 406. The fitting 406 may further comprise a locking mechanism (e.g., threads of a screw mechanism, etc.) and the fitting 412 may comprise a corresponding locking mechanism (e.g., complementary threads of a screw mechanism, etc.) that locks with the locking mechanism of the fitting 406.

For example, the fitting 406 may comprise a male-fitting, and the guide needle 410 may comprise the corresponding female-fitting to the male fitting. The probe 404 may be configured to fit through a lumen of the guide needle 410, and the guide needle 410 may slide along a length of the probe 104 and be secured to the fitting 406. For example, the probe 404 may have a diameter that is smaller than the diameter of the lumen of the guide needle 410.

Figure 5:
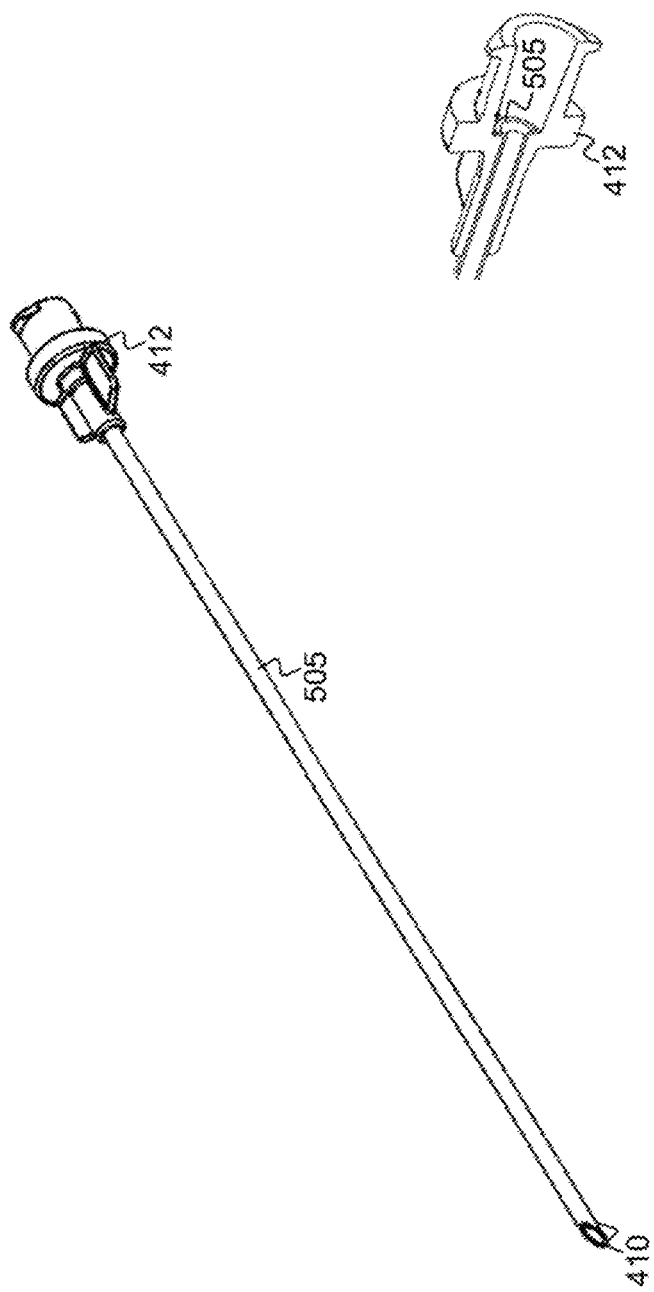
FIG. 5 illustrates an example of a guide needle configured to couple with the bipolar cautery device of FIG. 4, according to one embodiment.
Figure 6:
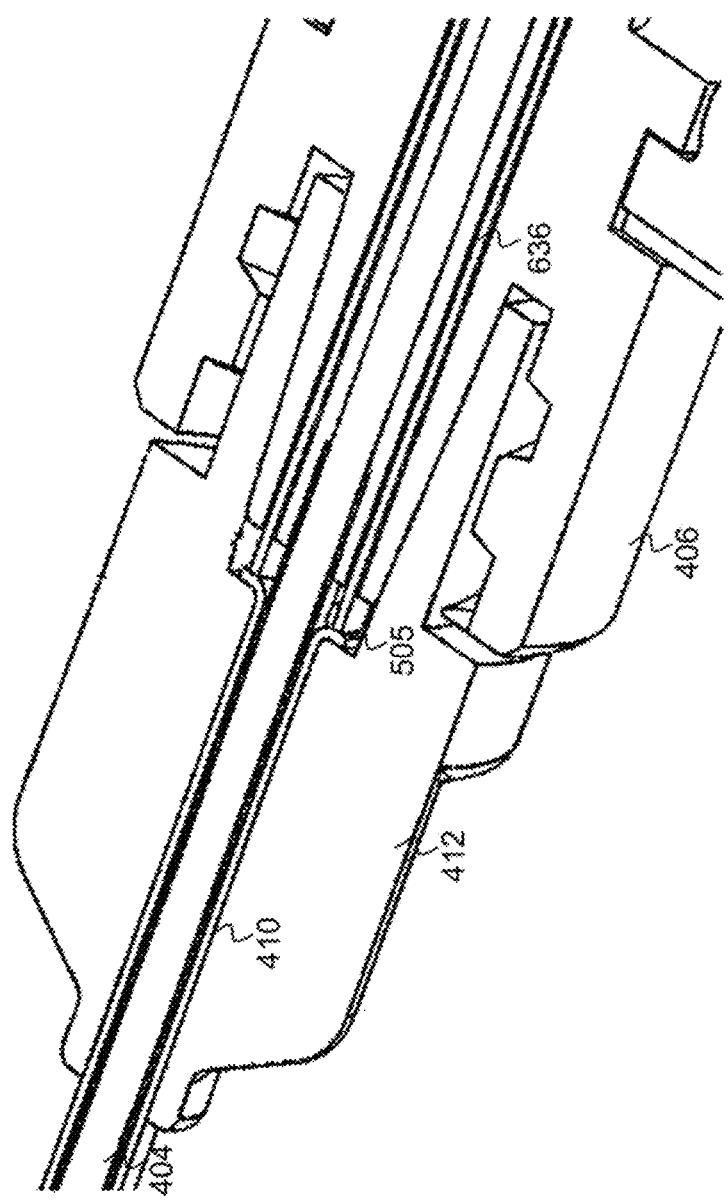
FIG. 6 illustrates a cutaway view of an example of a guide needle coupled with the bipolar cautery device of FIG. 4, according to one embodiment.

In some embodiments, the fitting 406 may be formed as a portion of the housing 402, as shown. Accordingly, the guide needle 410 may be configured to attach to the fitting 406 and be positioned along a length of the probe 104 at only a single position. Further, in some embodiments, the guide needle 410 may be a specialized guide needle. For example, the guide needle 410 may have a similar construction as a standard guide needle, and comprise a lumen and fitting 412 as discussed. For example, the needle portion of the guide needle 410 may be made of an appropriate metal. Further, the fitting 412 may be made of a plastic material. However, the guide needle 410 may further have an internal structure that allows the metal needle of the guide needle 410 to be electrically coupled to a voltage source in the housing 402. For example, as shown in FIG. 5, the needle portion 505 of the guide needle 410 may be exposed internally in the fitting 412. Further, as shown in FIG. 6, when the guide needle 410 is secured to the fitting 406, the needle portion 505 of the guide needle 410 may be in contact with a conductive element 636 (e.g., spring mounted metal contact) and therefore electrically coupled to the conductive element 636. The conductive element 636 may extend into the housing 402, and further be coupled to a voltage source within the housing 402. Accordingly, the guide needle 410 may be electrically coupled to the voltage source within the housing 402 when secured to the fitting 406.

Figure 7:
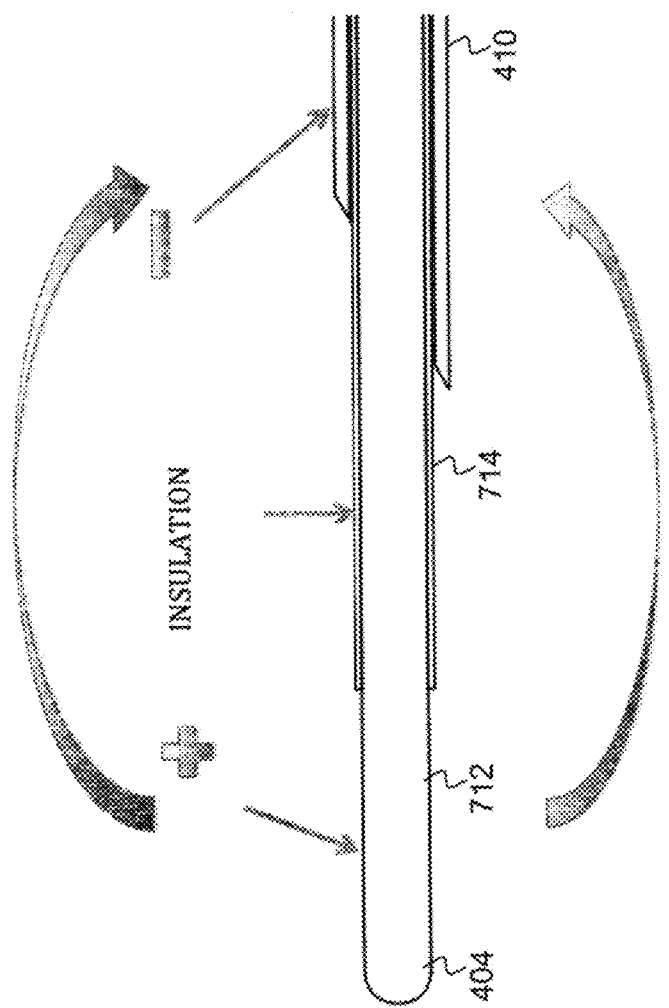
FIG. 7 illustrates an external view of a tip of the bipolar cautery device of FIG. 4 with a guide needle secured thereon, according to one embodiment.

The probe 404 may comprise a conductive element, such as a metal wire 712 (e.g., 18 gauge or 20 gauge wire) having a length that extends from the housing 402, as shown in FIG. 7. In some embodiments, the metal wire 712 may run the entire length of the probe 404 extending from the housing 402. The probe 404 may further comprise an insulator 714 (e.g., sterilized polyimide or other thin insulator) positioned around the metal wire 712. Accordingly, the insulator 714 may cover a portion of the metal wire 712. For example, the insulator 714 may comprise an insulating tube. The insulator 714 may be configured to run along a length of the metal wire 712 of the probe 404. Further, as shown in FIG. 7 the insulator 714 may not cover and therefore expose a portion (e.g., tip) of the metal wire 712. Accordingly, the insulator 714 may not run the entire length of the metal wire 712 extending from the housing 402, but instead a shorter length than the metal wire 712 so as to expose a portion of the metal wire 712. In particular, the insulator 714 may electrically insulate/isolate the metal wire 712 from the guide needle 410, when the probe 404 is inserted in the guide needle 410.

As discussed, the housing 402 may include a voltage source. The voltage source may comprise a first pole (e.g., positive or negative pole) and a second pole (e.g., the other of the positive and negative pole). The metal wire 712 may be electrically coupled to the first pole of the voltage source. Further, as discussed, the conductive element 636 within the housing 402 may be electrically coupled to the second pole of the voltage source. For example, each of the metal wire 712 and conductive element 636 may extend into the housing 402 and then be separately coupled by metal contacts, wires, traces, etc., to the voltage source.

As discussed, the metal needle 505 of the guide needle 410 may be electrically coupled with the conductive element 636 when secured to the cautery device 400. Accordingly, the guide needle 410 may be electrically coupled with the second pole of the voltage source.

Accordingly, when the probe 404 is inserted in the guide needle 410, and the guide needle 410 is inserted in tissue, a current may be generated by the voltage source and pass through the metal wire 712 and the guide needle 710 (e.g., via the conductive element 636) via the tissue, and therefore cauterize the tissue. As discussed above, the metal wire 712 and guide needle 410 may be insulated from each other via the insulator 714 to prevent a short in the circuit with the voltage source.

Figure 8:
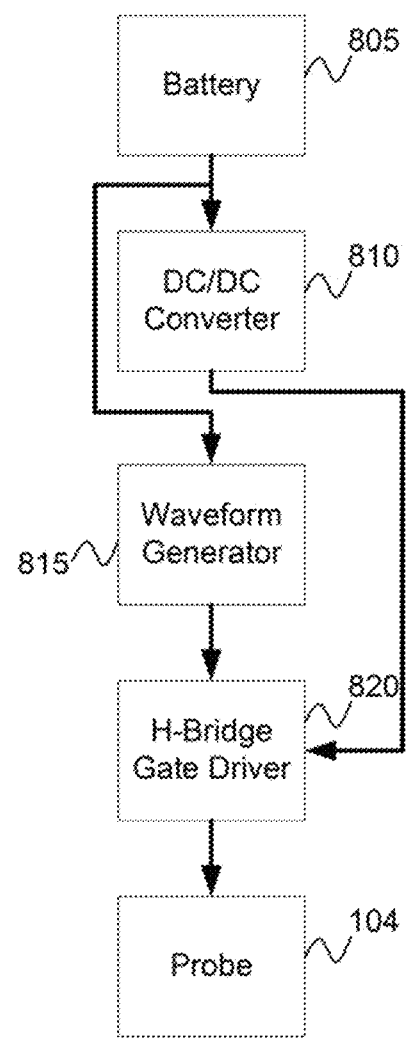
FIG. 8 illustrates a block diagram of a battery powered voltage source for a bipolar cautery device, according to one embodiment.

FIG. 8 illustrates a block diagram of a battery powered voltage source 800 for a bipolar cautery device, according to one embodiment. For example, the voltage source 800 may correspond to the voltage source of bipolar cautery device 100 or bipolar cautery device 400, or any other suitable bipolar cautery device. As shown, the voltage source 800 includes one or more batteries 805, a DC/DC converter 810, a waveform generator 815, and an H-bridge gate driver 820. The voltage source 800 further provides a voltage to the probe 104 as discussed herein. One or more components of the voltage source 800 may be implemented as discrete components or built as an integrated circuit (IC).

The battery 805 may be one or more physical batteries that have a base voltage. For example, the battery 805 may include five 3V batteries connected in series, thereby producing a 15V base voltage. A different number of batteries or different voltage level of batteries may be used. The battery 805 may be coupled to and supply the base voltage to a DC/DC converter 810. The DC/DC converter 810 may convert the base voltage level of the battery 805 to a higher voltage level. For example, the DC/DC converter 810 may convert a base voltage of 15V provided by the battery 805 to a higher voltage of 60V.

The battery 805 may further be coupled to and supply power to the waveform generator 815. In some embodiments, the DC/DC converter 810 may instead be coupled to and supply power to the waveform generator 815. The waveform generator 815 may be configured to convert a DC signal (from the battery 805 or the DC/DC converter 810) to an AC signal. In particular the waveform generator 815 may generate an AC signal at a particular frequency (e.g., 1 MHz, greater than 500 kHz, etc.). The waveform generator 815 may include an oscillator that oscillates at the particular frequency to generate the AC signal. The generated AC signal may be a periodic waveform that may have a selected shape (e.g., square wave, sinusoidal wave, triangle wave, sawtooth wave, etc.). In some embodiments, a square wave may be used to provide enhanced cauterization of tissue.

In some embodiments, the waveform generator 815 is further coupled to the H-bridge gate driver 820. The H-bridge gate driver 820 may further be coupled to the DC/DC converter 810 in some embodiments. The H-bridge gate driver 820 may be formed of switches (e.g., power field-effect transistors (FETs), such as, metal-oxide-semiconductor FETs (MOSFETs)). The H-bridge gate driver 820 may be configured to act as a relay for the power supplied from the DC/DC converter 810, and further convert the DC signal provided by the DC/DC converter 810 to an AC signal. For example, the H-bridge gate driver 820 may be configured to periodically switch the polarity of the DC signal supplied by the DC/DC converter 810 based on the AC signal from the waveform generator 815, which may act as a control signal for the H-bridge gate driver 820. Accordingly, the periodically switching polarity signal generated based on the DC signal by the H-bridge gate driver 820 may be an AC signal at the voltage level supplied by the DC/DC converter 810. Since the H-bridge gate driver 820 is controlled by the waveform generator 815, the AC signal generated by the H-bridge gate driver 820 may have the same shape as the AC signal generated by the waveform generator 815. The AC signal may then be applied to a probe (e.g., probe 104) of a cautery device to cauterize tissue. Accordingly, the voltage source 800 may be configured to convert a low voltage DC signal to a high voltage AC signal that can be supplied to a probe of a cautery device to cauterize tissue.

Figure 8A:
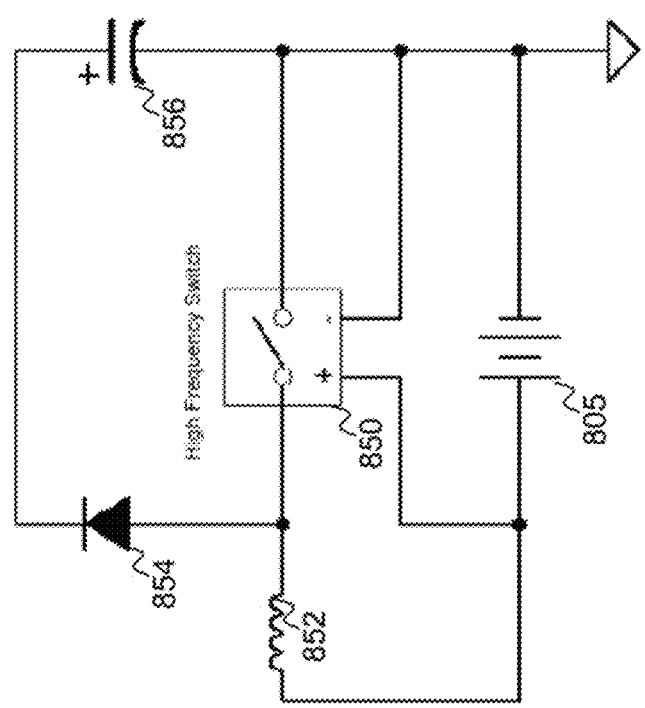
FIG. 8A illustrates a circuit diagram of a DC/DC converter for a bipolar cautery device, according to one embodiment.

FIG. 8A illustrates a circuit diagram of the DC/DC converter 810, according to one embodiment. The DC/DC converter 810 may be a voltage pump configured to generate a continuous high voltage DC signal from a low voltage signal. As shown, the DC/DC converter 810 is coupled to the battery 805. The H-bridge gate driver 820 may be coupled to a node at a first terminal of a capacitor 856 of the DC/DC converter that supplies the high voltage DC signal to the H-bridge gate driver 820.

As shown, the DC/DC converter 810 includes a switch 850. One terminal of the switch 850 may be coupled to a reference voltage (e.g., ground) and the other terminal of the switch 850 (referred to as the "positive terminal") may be coupled to the positive terminal of the battery 805. The switch 850 may be configured to open and close at a high frequency (e.g., 1 MHz, greater than 500 kHz, etc.). The positive terminal of the switch 850 may further be coupled to a first terminal of an inductor 852 and a first terminal of a diode 854. A second terminal of the inductor 852 may further be coupled to the positive terminal of the battery 805, and a second terminal of the diode 854 may further be coupled to the first terminal of the capacitor 856. A second terminal of the capacitor 856 may be coupled to the reference voltage. The DC/DC converter 810, accordingly, may be a type of RLC circuit.

In operation, as the switch 850 opens and closes the voltage across the capacitor 856 is increased as the capacitor 856 stores energy supplied from the battery 805. The diode 854 acts to keep current flowing in one direction to build charge on the capacitor 856. Further, the inductor 852 acts to keep the inertia of the current flowing to the capacitor 856 to charge the capacitor 856. Based on the size of the capacitor 856, the inductor 852, and the switching frequency of the switch 850, the voltage across the capacitor 856 is an increased multiple of the voltage across the battery 805. Further, the high speed switching frequency of the switch 850 allows the capacitor 856 to be charged faster than it is discharged while being used for supplying power for cauterization, thus producing a continuous power supply at the higher voltage.

Figure 9:
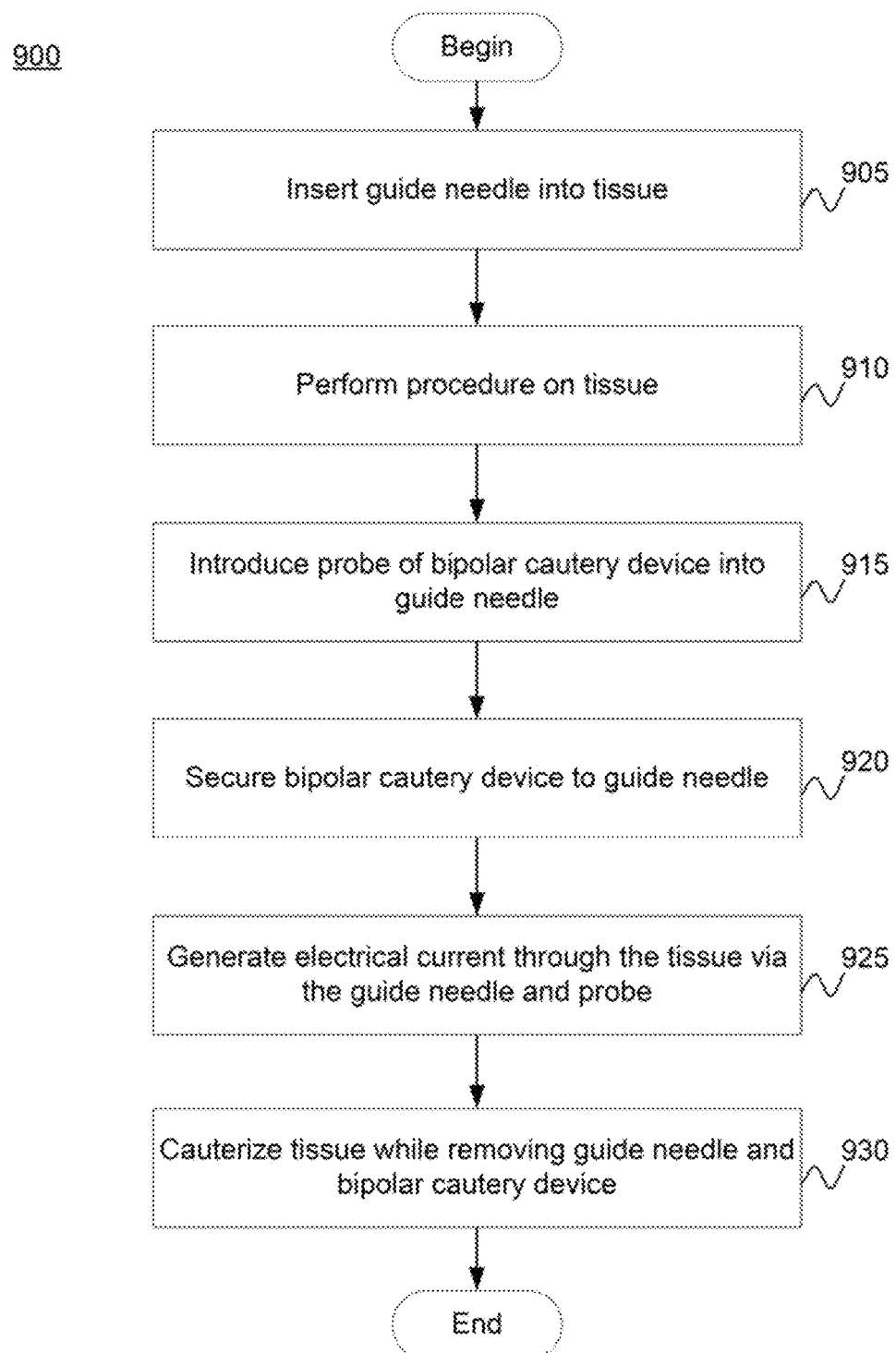
FIG. 9 illustrates an example of a method for cauterizing tissue using a bipolar cautery device, according to one embodiment.

FIG. 9 illustrates a method 900 for cauterizing tissue utilizing a bipolar cautery device, such as bipolar cautery device 100 or 400. The method begins at a step 905 where a guide needle is inserted into the tissue of a patient. Continuing, at step 910, a procedure may be performed at the tissue of the patient. For example, a minimally invasive biopsy may be performed at the tissue of the patient by inserting a biopsy needle through the lumen of the guide needle and removing the biopsy needle.

Further, at step 915, a probe of a bipolar cautery device may be introduced into the lumen of the guide needle. For example, the probe may be inserted into the lumen of the guide needle. Continuing, at step 920, the bipolar cautery device may be secured to the guide needle. At step 925, an electric current may be generated through the tissue via the guide needle and the probe. For example, a voltage source within the bipolar cautery device may be activated, and an electric current created through the tissue. At step 930, the bipolar cautery device secured to the guide needle may be removed from the patient, and the current may be applied to the tissue during the removal along a tract of the guide needle, thereby cauterizing the tissue along the tract.

Figure 10:
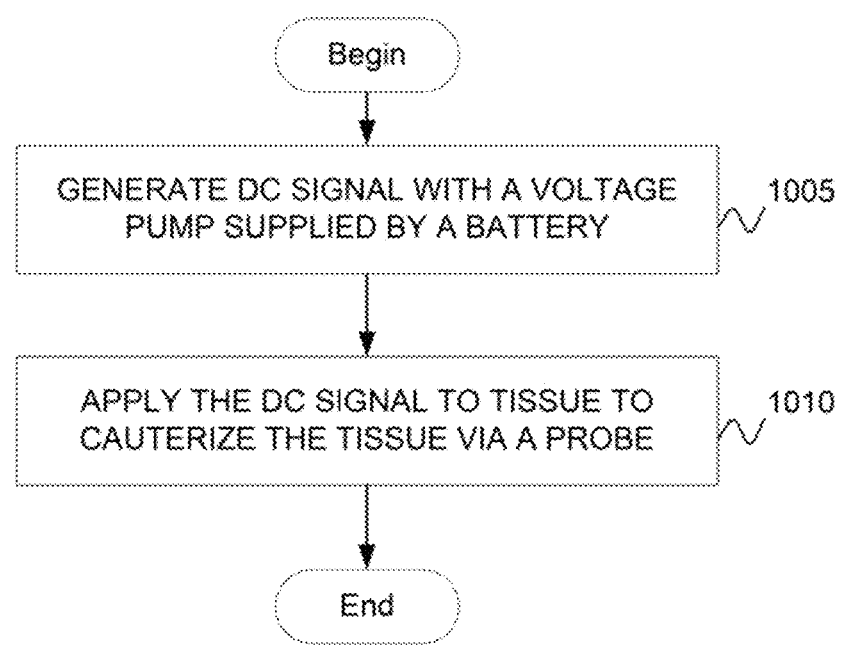
FIG. 10 illustrates an example of a method for cauterizing tissue using a bipolar cautery device, according to one embodiment.

FIG. 10 illustrates a method 1000 for cauterizing tissue utilizing a bipolar cautery device, such as bipolar cautery device 100 or 400. The method begins at a step 1005 where a DC signal is generated at a first voltage based on a second voltage supplied from a battery. The first voltage is higher than the second voltage. The DC signal may be generated, for example, by a voltage supply including the voltage pump and the battery. At 1010, the DC signal is applied via a probe to tissue in order to cauterize the tissue. The probe is electrically coupled to the voltage source. The probe includes a first electrically conductive element electrically coupled to a first pole of the voltage source. The probe further includes a second electrically conductive element coupled to a second pole of the voltage source.

In the preceding, reference is made to embodiments of the invention. However, the invention is not limited to specific described embodiments. Instead, any combination of the following features and elements, whether related to different embodiments or not, is contemplated to implement and practice the invention. Furthermore, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim (s). Likewise, reference to "the invention" shall not be construed as a generalization of any inventive subject matter disclosed herein and shall not be considered to be an element or limitation of the appended claims except where explicitly recited in a claim(s).

Aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples a computer readable storage medium include: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain, or store a program for use by or in connection with an instruction execution system, apparatus or device.

The flowchart and block diagrams in the Figures illustrate the architecture, functionality and operation of possible implementations of systems, methods and computer program products according to various embodiments of the present invention. In this regard, each block in the flowchart or block diagrams may represent a module, segment or portion of code, which comprises one or more executable instructions for implementing the specified logical function (s). In some alternative implementations the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

While the foregoing is directed to embodiments of the present invention, other and further embodiments of the invention may be devised without departing from the basic scope thereof, and the scope thereof is determined by the claims that follow.

What is claimed is:

1. A method of cauterizing using a handheld bipolar cautery device comprising a voltage source and a probe, the method comprising:
   introducing a biopsy needle into a lumen of a guide needle and tissue prior to introducing the probe into the lumen of the guide needle;
   introducing the probe into the lumen of the guide needle, wherein the probe is shaped to fit inside the lumen of the guide needle for percutaneous access to the tissue, wherein the probe is separate from the guide needle;
   generating, by the voltage source, an AC waveform comprising:
      generating a DC signal; and
      generating the AC waveform by periodically switching the polarity of the DC signal; and
   applying, by the probe, the AC waveform to the tissue to cauterize the tissue using current, wherein the probe comprises:
      a first electrically conductive element electrically coupled to a first pole of the voltage source, and
      a second electrically conductive element coupled to a second pole of the voltage source.

2. The method of claim 1, wherein the voltage source comprises a battery, a voltage pump, a waveform generator, and a gate driver, and wherein generating the AC waveform comprises
   generating, by the waveform generator, a signal at a frequency greater than 500 kHz, wherein generating the DC signal comprises generating, by the voltage pump, the DC signal based on a voltage provided by the battery, the DC signal having a voltage that is higher than the voltage provided by the battery, and wherein generating the AC waveform comprises generating, by the gate driver, the AC waveform by periodically switching the polarity of the DC signal based on the signal at the frequency greater than 500 kHz.

3. The method of claim 2, wherein the voltage pump comprises a RLC circuit and a switch, and wherein generating the DC signal comprises selectively electrically coupling and decoupling the battery to the RLC circuit at a frequency.

4. The method of claim 1, wherein the first electrically conductive element is exposed at one end of the probe, and wherein the guide needle is electrically coupled to the second electrically conductive element, wherein applying the AC waveform to the tissue to tissue to cauterize the tissue is performed via the first electrically conductive element and the guide needle.

\* \* \* \* \*